(12) United States Patent
Boskamp et al.

(10) Patent No.: US 10,504,711 B2
(45) Date of Patent: Dec. 10, 2019

(54) MASS SPECTROMETRIC METHOD AND MALDI-TOF MASS SPECTROMETER

(71) Applicant: Bruker Daltonik GmbH, Bremen (DE)

(72) Inventors: Tobias Boskamp, Worpswede (DE); Delf Lachmund, Bremen (DE)

(*) Notice: Subject to any disclaimer, the term of this patent is extended or adjusted under 35 U.S.C. 154(b) by 0 days.

(21) Appl. No.: 16/135,496

(22) Filed: Sep. 19, 2018

(65) Prior Publication Data
US 2019/0096652 A1    Mar. 28, 2019

(30) Foreign Application Priority Data

Sep. 22, 2017  (DE) ........................ 10 2017 008 885

(51) Int. Cl.
| | |
|---|---|
| *H01J 49/16* | (2006.01) |
| *H01J 49/00* | (2006.01) |
| *H01J 49/40* | (2006.01) |
| *G01N 33/68* | (2006.01) |
| *G06K 9/62* | (2006.01) |

(52) U.S. Cl.
CPC ........ *H01J 49/164* (2013.01); *G01N 33/6851* (2013.01); *G06K 9/6298* (2013.01); *H01J 49/004* (2013.01); *H01J 49/0036* (2013.01); *H01J 49/40* (2013.01)

(58) Field of Classification Search
USPC ................................................. 250/282, 281
See application file for complete search history.

(56) References Cited

U.S. PATENT DOCUMENTS

| | | | | |
|---|---|---|---|---|
| 2004/0096917 A1* | 5/2004 | Ivey | ..................... | C12Q 1/6837 435/7.32 |
| 2004/0157242 A1* | 8/2004 | Ivey | ..................... | C12Q 1/6883 435/6.16 |
| 2004/0195500 A1 | 10/2004 | Sachs et al. | | |
| 2017/0352525 A1 | 12/2017 | Ikegami et al. | | |

FOREIGN PATENT DOCUMENTS

| | | |
|---|---|---|
| EP | 2388797 A1 | 11/2011 |
| WO | 2014147404 A1 | 9/2014 |
| WO | 2016103312 A1 | 6/2016 |

OTHER PUBLICATIONS

Caprioli, R.M., et al. "Molecular Imaging of Biological Samples: Localization of Peptides and Proteins Using MALDI-TOF MS", Anal Chem (1997) 69, pp. 4751-4760.
Sören-Oliver Deininger, et al. "Normalization in MALDI-TOF imaging datasets of proteins: practical considerations", Anal Bioanal Chem (Mar. 2011) 401:167-181.

* cited by examiner

*Primary Examiner* — Kiet T Nguyen
(74) *Attorney, Agent, or Firm* — Benoit & Côté Inc.

(57) ABSTRACT

A number of standard methods exist for normalizing MALDI-TOF data, but they are not able to compensate adequately for the observed technical variability. The invention creates an improved normalization method for MALDI-TOF mass spectrometry data. This is achieved by an intensity profile normalization, where, by way of example, 1) Firstly, an intensity profile is formed for each individual spectrum, and this intensity profile describes the statistical distribution of the intensity values within different mass ranges;

2) Then an average reference profile is formed for an ensemble of spectra;

(Continued)

3) Finally, the individual spectra are transformed in such a way that their intensity profiles correspond to the reference profile.

14 Claims, 2 Drawing Sheets

MASS SPECTROMETRIC METHOD AND MALDI-TOF MASS SPECTROMETER

BACKGROUND OF THE INVENTION

Field of the Invention

The invention relates to a mass spectrometric method to evaluate MALDI-TOF mass spectrometry data for the analysis of macromolecules from biological samples and a MALDI-TOF mass spectrometer for performing such a method.

Description of the Related Art

In matrix-assisted laser desorption/ionization time-of-flight (MALDI-TOF) mass spectrometry, a suitably prepared biological tissue sample is coated with a matrix solution and exposed to laser radiation in a vacuum (see Caprioli RM, Farmer TB, and Gile J., *Molecular imaging of biological samples: Localization of peptides and proteins using MALDI-TOF MS,* Analytical Chemistry, 69(23):4751-4760, 1997. doi:10.1021/ac970888i). In this process, biological macromolecules are ionized and extracted from the tissue. The ionized macromolecules typically have a positive charge. The ions are accelerated in an electric field and recorded by a detector. The m/z value, i.e. the mass-to-charge ratio of the ionized molecule, can be determined from the time of flight of the ions from the tissue to the detector, which is itself determined from the ionizing laser pulse and the detector signal. The relative number of recorded ions (spectral intensity), as a function of the m/z value, represents a mass spectrum. Assuming a single positive ionization of the molecules, the m/z value is identical to the mass of the ionized molecule. The mass of the molecules is given in daltons (Da) as a multiple of the atomic mass unit (1 Da=1 amu).

In the acquisition of MALDI-TOF mass spectrometry data from biological tissue sections, a large amount of information on the proteomic structure of the tissue samples is obtained. At the same time, the measurement is subject to a number of possible interferences, which can lead to distortions and thus to corruption of the information gained. The variability of these interferences is relatively high, even under identical measuring conditions, and therefore the results of several measurements can often only be compared to a limited extent. If the measurements are conducted in different laboratories or under conditions which are not precisely identical, a comparison is often rendered impossible.

A number of standard methods exist for correcting such interferences and normalizing MALDI-TOF data, but they are not able to compensate adequately for the observed technical variability. Moreover, there is a lack of objective and easily applicable benchmarks for assessing the extent to which two different measurements can be compared.

A frequently observed effect of technical variability within the measured data consists in systematic differences in respect of the measured spectral intensities. Such differences occur even under carefully controlled experimental conditions, and make a comparative assessment of two measurements more difficult. In many cases, conventional methods for correcting these intensity differences are inadequate.

The measured intensities for the m/z values represent only relative values with respect to each other, and these are only comparable within a single spectrum. The complex desorption and ionization process means that the absolute intensity measurements differ greatly between two spectra, which is why MALDI-TOF spectra are usually normalized before being evaluated further. The most commonly used normalizations are the Total Ion Count (TIC) and the median normalization (see for example, Deininger SO, Cornett DS, Paape R, Becker M, Pineau C, Rauser S, Walch A, Wolski E., *Normalization in MALDI-TOF imaging datasets of proteins: Practical considerations, Analytical and Bioanalytical Chemistry,* 401(1):167-181, 2011. doi: 10.1007/s00216-011-4929-z, and Deininger SO, Wolski E., *Normalization of mass spectra acquired by mass spectrometric imaging,* 2011, European patent application EP 2 388 797 (A1)).

With all the normalizations hitherto proposed, all the intensities of a spectrum are multiplied by a common factor, which is determined individually for each spectrum. In practice, however, it is observed that the effects which lead to different absolute intensities in two spectra have different effects in different regions of the mass axis. The normalization cannot compensate for these differences, and therefore significant differences in the intensity levels of the individual spectra remain, depending on the mass region. Examples of such differences in intensity levels between individual spectra (spectrum 1 and spectrum 2) for different mass ranges are shown in FIG. 1a, FIG. 1b and FIG. 1c.

These normalization methods transform a spectrum with reference to an arbitrary reference value chosen the same for all spectra (e.g. median=1 in the case of median normalization). The normalization is therefore always applied to each spectrum individually, independently of the other spectra of the same or further measurements.

In contrast, the term "cross-normalization" designates a transformation which transforms two or more spectra such that they are as similar or comparable as possible in respect of specific characteristics, without setting an external reference point for this. A cross-normalization can therefore only ever be carried out for an ensemble of spectra.

Following the example of median normalization, the term cross-normalization could also be used when two spectra are each multiplied by a factor in such a way that the medians of the intensities correspond to the average value of the original medians, for example. This form of cross-normalization would, of course, have no advantage over the usual median normalization, however.

SUMMARY OF THE INVENTION

The present invention is directed to creating a better normalization method for MALDI-TOF mass spectrometry data, particularly for measured spectral intensities.

To achieve this, a mass spectrometric method for the analysis of macromolecules, such as peptides, from biological samples is proposed using a MALDI-TOF mass spectrometer, where the mass spectrometry data, particularly the spectral intensities of the spectra, are normalized by means of an intensity profile normalization, by way of example in the following steps:

1) Firstly, an intensity profile is formed for each individual spectrum, and this intensity profile describes the statistical distribution of the intensity values within different mass ranges.

2) Then an average reference profile is formed for an ensemble of spectra.

3) Finally, the individual spectra are transformed in such a way that their intensity profiles correspond to the reference profile.

A further proposal according to the invention is that the intensity profile of a spectrum is formed by first specifying a subdivision of an abscissa axis of the spectrum, preferably a mass axis, into sub-intervals I, particularly 4-8 intervals of the same width.

Advantageously, a further embodiment of the present invention can provide for a quantile scale with a sequence of p-values within the interval (0,1) to be specified.

Moreover, it is conceivable that the quantile scale contains 10-20 reference points, which are closer together at the ends of the interval than within it and cover the range $0.1<p<0.999$.

Furthermore, one aspect of the invention can be considered to be that for each sub-interval I of the abscissa axis of the spectrum, particularly the mass axis, the spectral intensities are combined and the respective empirical p quantiles for the points p of the quantile scale are calculated.

In particular, the invention can provide for the logarithms of the quantile values to be computed and the differences between successive values to be formed.

Finally, an advantageous embodiment of the method according to the invention can be considered to be the formation of a reference profile for an ensemble of MALDI spectra, and that in this reference profile an arithmetic mean of the individual intensity profiles is determined element by element, but undefined entries are not taken into account in the averaging.

An additional provision is that, for the normalization of an individual spectrum to the reference profile, the reference profile is transformed back into quantile values by cumulative summing of the matrix entries of the reference profile row by row and by calculating their antilogarithm, ignoring undefined entries.

According to a further example embodiment, it is conceivable for the quantile values of the individual spectrum which is being normalized and of the reference profile to be considered as reference points of a transfer function, between which the values are suitably interpolated, especially linearly or with spline functions, while outside the intensity range specified by the reference points, the transfer function is continued at a constant value.

Finally, the embodiment can provide for the normalized spectrum to be generated by applying the transfer function to the intensity values of the individual spectrum.

A MALDI-TOF mass spectrometer for achieving the objective stated in the introduction is also provided to carry out a method as described above.

BRIEF DESCRIPTION OF THE DRAWINGS

Further measures and characteristics of the invention and example embodiments of the invention are explained below in more detail with the aid of drawings. They show.

DETAILED DESCRIPTION

In the following, a method for cross-normalization of the spectral intensities in MALDI-TOF mass spectrometry data is described, with which several datasets are modified such that they can be better compared with each other and characteristic spectral features can be extracted more easily. The method is based on the statistical modeling of the intensities measured in a spectrum as a function of the measured mass.

To achieve this, an intensity profile is first formed for each individual spectrum, said profile describing the statistical distribution of the intensity values within different mass ranges. An average reference profile is then formed for an ensemble of spectra, and the individual spectra are transformed in such a way that their intensity profiles correspond to the reference profile. In the following, the term intensity profile normalization is used for this method.

Figure 1A:
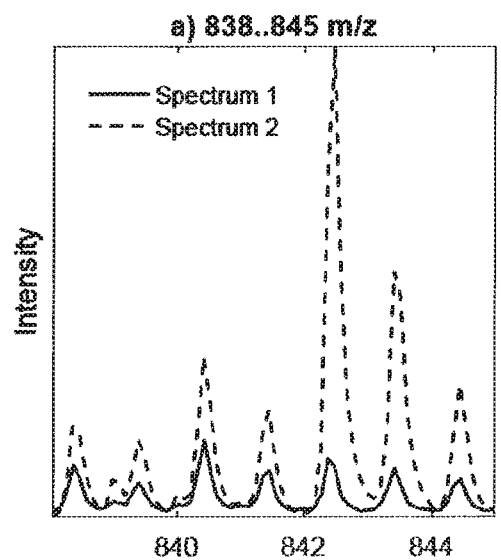
FIG. 1a—Example of differences in the intensity levels of individual spectra.
Figure 1B:
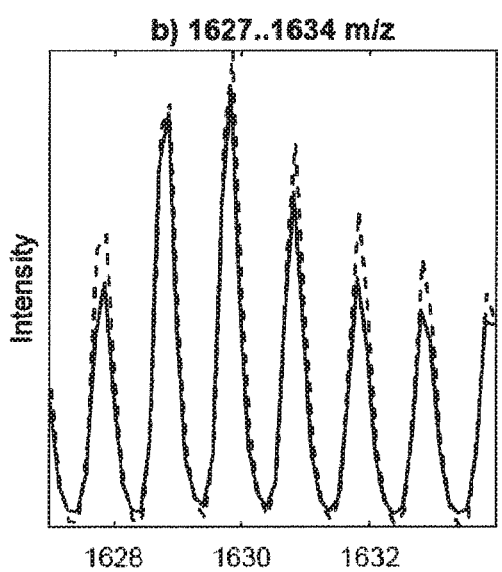
FIG. 1b—Example of differences in the intensity levels of individual spectra.
Figure 1C:
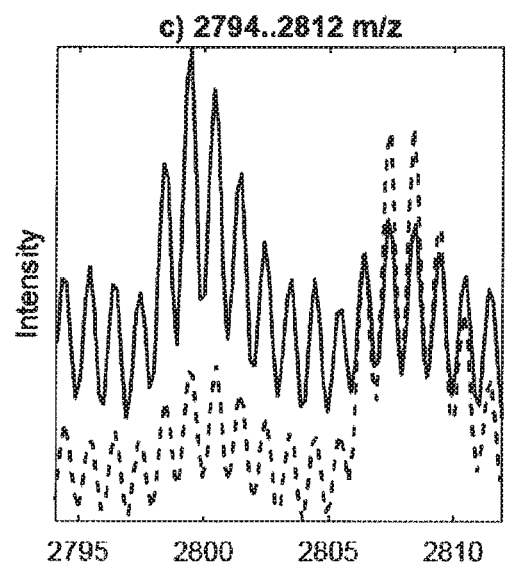
FIG. 1c—Example of differences in the intensity levels of individual spectra.
Figure 2:
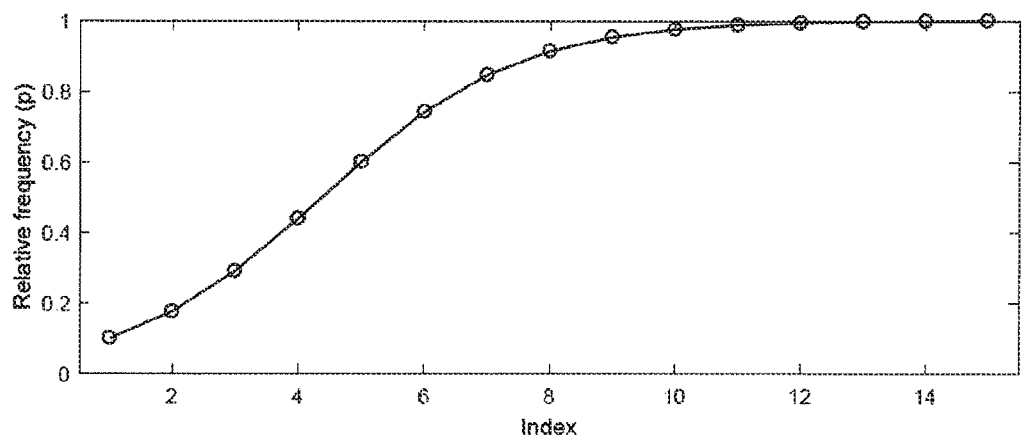
FIG. 2—An exemplary quantile scale with 15 reference points.

The intensity profile of a spectrum is formed by first specifying a subdivision of the mass axis into sub-intervals, typically 4-8 intervals of the same width. Moreover, a quantile scale is specified, i.e. a sequence of p-values within the interval (0,1). The quantile scale typically contains 10-20 reference points, which are closer together at the ends of the interval than within it, and cover the range $0.1<p<0.999$ (FIG. 2).

The spectral intensities are now combined for each sub-interval I of the mass axis, and the respective empirical p quantiles for the points p of the quantile scale are calculated. In a next step, the logarithms of the quantile values are computed and the differences between successive values are formed. This transformation means that the resulting profile vector does not depend on the spectral intensities having a linear scale, e.g. as a consequence of a previous normalization according to one of the standard methods (see above). The intensity profile of a spectrum then consists of a matrix in which the individual rows each contain the profile vectors belonging to one sub-interval.

Since spectral intensities can assume the value 0, this also applies to the quantile values at the lower end of the quantile scale. The logarithms of these values and the corresponding matrix entries of the intensity profile cannot be computed in this case, and are treated as undefined.

For an ensemble of MALDI spectra, a reference profile is formed in which the arithmetic mean of the individual intensity profiles is determined element by element. Undefined entries are not taken into account in the averaging.

To normalize an individual spectrum to the reference profile, the reference profile is first transformed back into quantile values by cumulative summing of the matrix entries of the reference profile row by row and by calculating their antilogarithm. Undefined entries are again ignored. The quantile values of the individual spectrum which is being normalized and of the reference profile are then considered as reference points of a transfer function, between which the values are suitably interpolated (e.g. linearly or using spline functions). Outside the intensity range specified by the reference points, the transfer function is continued at a constant value. The normalized spectrum is obtained by applying the transfer function to the intensity values of the individual spectrum.

The invention claimed is:

1. A mass spectrometric method for the analysis of macromolecules from biological samples using a MALDI-TOF mass spectrometer, where the spectral intensities of the spectra from the mass spectrometry data are normalized by means of an intensity profile normalization, including the following steps:
   (i) forming an intensity profile for each individual spectrum, which intensity profile describes the statistical distribution of the intensity values within different mass ranges;

(ii) forming an average reference profile for an ensemble of spectra; and (iii) transforming the individual spectra in such a way that their intensity profiles correspond to the reference profile.

2. The mass spectrometric method according to claim 1, wherein the intensity profile of a spectrum is formed by first specifying a subdivision of an abscissa axis of the spectrum into sub-intervals I.

3. The mass spectrometric method according to claim 2, wherein the abscissa axis is a time-of-flight axis or mass axis.

4. The mass spectrometric method according to claim 2, wherein the sub-intervals I comprise 4-8 intervals of equal width.

5. The mass spectrometric method according to claim 2, wherein a quantile scale is specified with a sequence of p-values within the interval (0,1).

6. The mass spectrometric method according to claim 5, wherein the quantile scale spans 10-20 reference points, which are closer together at the ends of the interval than within it and cover the range $0.1 < p < 0.999$.

7. The mass spectrometric method according to claim 6, wherein for each sub-interval I of the abscissa axis of the spectrum, the spectral intensities are combined and the respective empirical p quantiles for the points p of the quantile scale are calculated.

8. The mass spectrometric method according to claim 7, wherein the logarithms of the quantile values are computed and the differences between successive values are formed.

9. The mass spectrometric method according to claim 1, wherein a reference profile is formed for an ensemble of MALDI spectra, and in this reference profile an arithmetic mean of the individual intensity profiles is determined element by element, where undefined entries are not taken into account in the averaging.

10. The mass spectrometric method according to claim 9, wherein for the normalization of an individual spectrum to the reference profile, the reference profile is transformed back into quantile values by cumulative summing of the matrix entries of the reference profile row by row and by calculating their antilogarithm, ignoring undefined entries.

11. The mass spectrometric method according to claim 10, wherein the quantile values of the individual spectrum to be normalized and of the reference profile are considered to be reference points of a transfer function, between which the values are suitably interpolated, while outside the intensity range specified by the reference points, the transfer function is continued at a constant value.

12. The mass spectrometric method according to claim 11, wherein the interpolation is carried out linearly or using spline functions.

13. The mass spectrometric method according to claim 11, wherein the normalized spectrum is produced by applying the transfer function to the intensity values of the individual spectrum.

14. A MALDI-TOF mass spectrometer having a control unit for the analysis of macromolecules from biological samples that is configured for using a method according to claim 1.

* * * * *